(12) United States Patent
Xu et al.

(10) Patent No.: US 8,953,911 B1
(45) Date of Patent: Feb. 10, 2015

(54) SPECTROSCOPIC IMAGING PROBES, DEVICES, AND METHODS

(75) Inventors: Chenyang Xu, Medford, MA (US); Joseph M. Schmitt, Andover, MA (US)

(73) Assignee: Lightlab Imaging, Inc., Westford, MA (US)

( * ) Notice: Subject to any disclaimer, the term of this patent is extended or adjusted under 35 U.S.C. 154(b) by 348 days.

(21) Appl. No.: 13/284,369

(22) Filed: Oct. 28, 2011

(51) Int. Cl.
*G02B 6/26* (2006.01)
*G02B 6/00* (2006.01)

(52) U.S. Cl.
CPC ...... *G02B 6/26* (2013.01); *G02B 6/00* (2013.01)
USPC .............................................. 385/12; 385/31

(58) Field of Classification Search
CPC ............. G02B 6/26; G02B 6/262; G02B 6/00
USPC ................... 385/12, 31, 28, 15, 116, 117
See application file for complete search history.

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,465,147 A | 11/1995 | Swanson | |
| 5,509,093 A | 4/1996 | Miller et al. | |
| 5,619,368 A | 4/1997 | Swanson | |
| 5,748,598 A | 5/1998 | Swanson et al. | |
| 5,784,352 A | 7/1998 | Swanson et al. | |
| 5,956,355 A | 9/1999 | Swanson et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |

(Continued)

FOREIGN PATENT DOCUMENTS

WO  2012176191  12/2012

OTHER PUBLICATIONS

Li et al., "Hybrid Intravascular Ultrasound and Optical Coherence Tomography Catheter for Imaging of Coronary Atherosclerosis", Catherization and Cardiovascular Interventions 00:000-000 (2012) pp. 1-14.

(Continued)

*Primary Examiner* — Charlie Peng
*Assistant Examiner* — Mary El Shammaa
(74) *Attorney, Agent, or Firm* — K&L Gates LLP

(57) ABSTRACT

In part, the invention relates to a single clad fiber to multi-clad optical fiber connector for use in applying excitation light to a sample and obtaining reflected light from the sample. The connector can include a dual clad optical fiber portion and a single clad optical fiber portion in optical communication with the dual clad optical fiber portion. In one embodiment, a core of the dual clad optical fiber portion and a core of the single clad optical fiber portion have substantially similar indices of refraction. In one embodiment, excitation light is propagated by the core of the dual clad optical fiber. Further, in one embodiment, light reflected by the sample is propagated by the first cladding layer of the dual clad optical fiber portion.

8 Claims, 15 Drawing Sheets
(5 of 15 Drawing Sheet(s) Filed in Color)

(56) References Cited

U.S. PATENT DOCUMENTS

| | | |
|---|---|---|
| 6,570,659 B2 | 5/2003 | Schmitt |
| 6,706,004 B2 | 3/2004 | Tearney et al. |
| 6,879,851 B2 | 4/2005 | McNamara et al. |
| 6,891,984 B2 | 5/2005 | Petersen et al. |
| 6,904,199 B2 | 6/2005 | Zuluaga |
| 7,208,333 B2 | 4/2007 | Flanders et al. |
| 7,231,243 B2 | 6/2007 | Tearney et al. |
| 7,241,286 B2 | 7/2007 | Atlas |
| 7,382,464 B2 | 6/2008 | Everett et al. |
| 7,414,779 B2 | 8/2008 | Huber et al. |
| 7,415,049 B2 | 8/2008 | Flanders et al. |
| 7,447,408 B2 | 11/2008 | Bouma et al. |
| 7,625,366 B2 | 12/2009 | Atlas |
| 7,809,226 B2 | 10/2010 | Bouma et al. |
| 7,813,609 B2 | 10/2010 | Petersen et al. |
| 7,848,791 B2 | 12/2010 | Schmitt et al. |
| 7,872,759 B2 | 1/2011 | Tearney et al. |
| 7,916,387 B2 | 3/2011 | Schmitt et al. |
| 7,935,060 B2 | 5/2011 | Schmitt et al. |
| 8,290,228 B2 | 10/2012 | Cohen et al. |
| 8,298,147 B2 | 10/2012 | Huennekens et al. |
| 8,463,007 B2 | 6/2013 | Steinberg et al. |
| 8,542,900 B2 | 9/2013 | Tolkowsky et al. |
| 2002/0161351 A1 | 10/2002 | Samson et al. |
| 2003/0028100 A1 | 2/2003 | Tearney et al. |
| 2004/0131322 A1 | 7/2004 | Ye et al. |
| 2005/0201662 A1 | 9/2005 | Petersen et al. |
| 2006/0095065 A1 | 5/2006 | Tanimura et al. |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2010/0094127 A1 | 4/2010 | Xu |
| 2010/0160764 A1 | 6/2010 | Steinberg et al. |
| 2010/0160773 A1 | 6/2010 | Cohen et al. |
| 2010/0172556 A1 | 7/2010 | Cohen et al. |
| 2010/0253949 A1 | 10/2010 | Adler et al. |
| 2011/0007315 A1 | 1/2011 | Petersen et al. |
| 2011/0071404 A1 | 3/2011 | Schmitt et al. |
| 2011/0071405 A1 | 3/2011 | Judell et al. |
| 2011/0101207 A1 | 5/2011 | Schmitt |
| 2011/0151980 A1 | 6/2011 | Petroff |
| 2011/0157686 A1 | 6/2011 | Huber et al. |
| 2011/0172511 A1 | 7/2011 | Schmitt et al. |
| 2011/0178413 A1 | 7/2011 | Schmitt et al. |
| 2011/0216325 A1 | 9/2011 | Schmitt |
| 2011/0228280 A1 | 9/2011 | Schmitt et al. |
| 2012/0230565 A1 | 9/2012 | Steinberg et al. |

OTHER PUBLICATIONS

Anderson et al., "Feasibility of Two-Dimensional Color Imaging in Coronary Vessels Using a Single-Mode Fiber Catheter", IEEE Xplore 18:54:24 (2010) pp. 325-326.

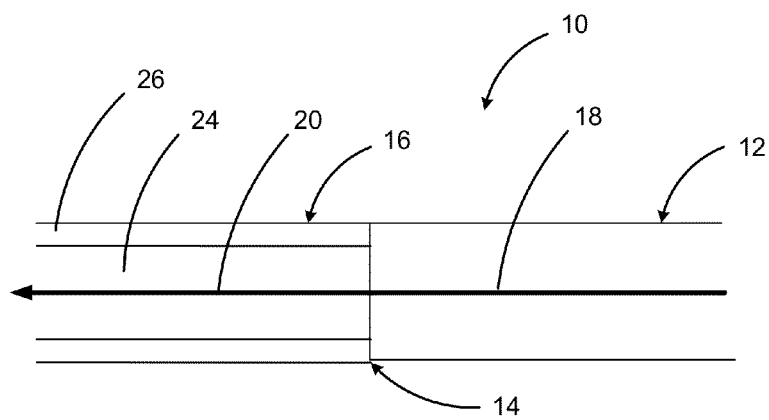
Fig. 1A
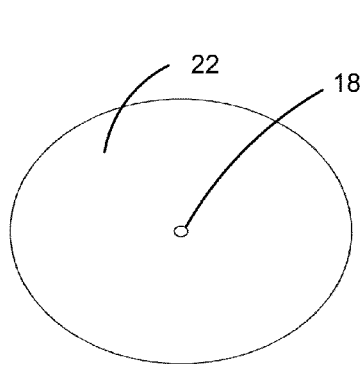 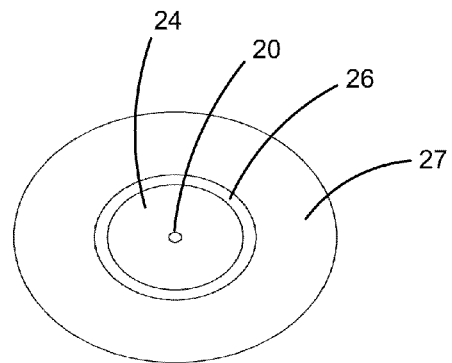
Fig. 1B        Fig. 1C

SPECTROSCOPIC IMAGING PROBES, DEVICES, AND METHODS

FIELD OF INVENTION

This invention pertains generally to imaging probes and more specifically to probes having color spectroscopic imaging and tomographic capabilities suitable for use in various applications such as medical imaging, fiber-optic sensing, and industrial inspection.

BACKGROUND

Fiber optic sensing has been used for probing remote areas that have limited spatial clearance. It is particularly useful in biomedical research for probing internal cavities (e.g., body lumens) and in industrial applications for monitoring hard-to-reach areas such as the inside of a small curved tube. One particular area of fiber optic sensing relates to imaging. A fiber bundle can be used to transmit images coherently along the bundle. This approach is used in endoscopic applications. However, fiber bundles often have a relatively large size, can be stiff and are generally expensive.

Another possible arrangement is to reconstruct an image by scanning a single fiber over a sample of interest. Single-fiber imaging is particularly attractive for certain applications, such as intravascular scanning, because of the small outer diameter of the single fiber. Single-mode fibers are used in applications that require coherent transmission of light, such as low coherence interferometry and optical coherence tomography (OCT). In contrast, multimode fibers are used in applications that do not require coherent transmission of light, but need high collection efficiency, such as fluorescence imaging or Raman spectroscopy.

One technical difficulty of performing single-fiber imaging is the separation of the excitation light and the collection light. Because the excitation light usually is much more intense than collected light, the collected signals are harder to detect relative to the excitation light reflected from various optical interfaces. As a result, it is difficult to obtain real-time color images of the vessel wall in the visible light range using existing optical coherence tomography (OCT) systems. OCT also typically cannot measure light produced by incoherent optic processes such as fluorescence.

A need therefore exists for imaging methods and probes that can provide real-time color images that are suitable for use with an OCT system. The present invention addresses this need and others.

SUMMARY OF THE INVENTION

The invention provides, in part, an apparatus for obtaining color and spectroscopic information using an imaging probe having a fixed or rotatable fiber. More specifically, devices, systems, and methods are provided for obtaining OCT and/or color images from a sample by using an optical fiber. The system can be used for obtaining OCT data simultaneously along with other optical data such as fluorescence, Raman, and two-photon signals.

One embodiment of the present invention provides methods for obtaining color reflectance signals through a probe that includes one or more optical fibers. Suitable optical fibers include single-core fibers having a single cladding layer (i.e., a single clad fiber (SCF)) or multiple cladding layers (MCF) such as a dual clad fiber (DCF) which has two cladding layers.

In some embodiments, light composed of multiple wavelengths is launched (or injected) from a light source directly or indirectly (e.g., via another fiber) into the core of a dual clad fiber (DCF) fiber that is optically connected to a probe. Injected light travels down the fiber towards the probe until the injected light exits the probe and impinges on the sample. Light reflected by the sample is then collected by the probe and is transmitted back through the fiber towards the light source through the inner cladding of the DCF. Light passing back through the fiber is directed to one or more detectors that receive an optical signal or an electrical signal correlated to the optical signal. The collected signals are processed to subsequently form a colored or hyperspectral image of the sample. The signal detection or collection steps can be performed sequentially with one detector or in parallel with multiple detectors.

Another embodiment of the present invention combines color reflectance imaging with OCT. OCT is used to obtain the distances of the reflections from the sample to the probe. From these distances, such as penetration distances into a lumen, a 3D surface can be rendered. The color or hyperspectral reflectance images are then overlaid onto the 3D surface to reconstruct a 3D color surface or a 3D hyperspectral image.

Some embodiments of the invention provide methods to construct and use the fiber-based devices that combine spectral data and OCT to generate a color image of a body object such as an eye, tissue sample, or a lumen such as a blood vessel.

Other embodiments of the present invention provide techniques that couple light into and out of a cladding layer of a DCF (or multiple-clad, multiple-core fiber). In some embodiments, the techniques involve first connecting a matching single-core fiber (SCF) that does not have a second outer clad layer to the DCF. The matching SCF has similar geometry, core composition, and cladding layers as the multiple clad fiber except that the matching SCF lacks the outermost cladding layer of the DCF. Next the combined matched fiber is surrounded with index-matching material and the applicable optical apparatus either to inject or collect light.

In one aspect, the invention relates to an optical system that includes a single clad to multi-clad optical fiber connector comprising a dual clad optical fiber portion and a single clad optical fiber portion. In one embodiment, the dual clad optical fiber portion includes a first core portion, a first cladding layer adjacent the first core portion, and a second cladding layer adjacent the first cladding layer. The first cladding layer and the second cladding layer have lower refractive indices than the first core portion. The single clad optical fiber portion is in optical communication with the dual clad optical fiber portion. The single clad optical fiber portion includes a second core portion and a first cladding layer adjacent the second core portion. The second core portion and the first core portion have substantially similar indices of refraction and together form a core. The first core portion of the dual clad optical fiber is configured to propagate excitation light to a sample. The first cladding layer of the dual clad optical fiber portion is configured to collect light scattered from the sample. In another embodiment, the single clad optical fiber portion comprises an outer surface and has a longitudinal axis. The outer surface defines an emission region wherein light propagating in the first cladding layer exits the emission region at an angle relative to the longitudinal axis.

In another embodiment, the optical system further includes a light source in optical communication with the single clad optical fiber portion; a probe in optical communication with the dual clad optical fiber portion; and a detector in optical communication with the single clad to multi-clad optical fiber connector. The detector detects light reflected by the sample and ejected by the first cladding layer of the dual clad optical fiber portion. In yet another embodiment, the optical system further includes an OCT subsystem; and a beam splitter/combiner, the beam splitter/combiner in the optical path between the light source and the probe and in the optical path between the OCT subsystem and the probe. Light from the OCT subsystem and light from the light source are combined prior to being transmitted to the probe. In still yet another embodiment, the optical system further includes an optical coupler for coupling light from the light source into the second core portion of the single clad optical fiber portion. In another embodiment, the optical system further includes a rotatable optical coupler in the optical path between the optical coupler for coupling light from the light source into the second core portion of the single clad optical fiber portion and the probe. In still yet another embodiment of the optical system, the rotatable optical coupler in the optical path between the optical coupler for coupling light from the light source into the second core of the single clad optical fiber portion and the probe is positioned adjacent the optical coupler.

In one embodiment, the rotatable optical coupler is in the optical path between the optical coupler for coupling light from the light source into the second core portion of the single clad optical fiber portion and the probe is positioned within the optical path defined by the single clad fiber. In another embodiment, the rotatable optical coupler in the optical path between the optical coupler for coupling light from the light source into the second core portion of the single clad optical fiber portion and the probe is positioned within the optical path defined by the double clad fiber. In still yet another embodiment, the rotatable optical coupler in the optical path between the optical coupler for coupling light from the light source into the second core portion of the single clad optical fiber portion and the probe is a part of the single clad to multi-clad optical fiber connector. In another embodiment, the optical system further includes an optical coherence tomography probe having a reflector configured for directing light from the core to the sample and receiving light from the sample into the first cladding layer.

In one embodiment, the system further includes a rotatable optical coupler in the optical path between the light source and the probe and wherein the probe rotates. In another embodiment, the optical system further includes an optical coherence tomography subsystem configured to receive (i) light or (ii) a signal derived from light returning along the core from the sample.

In another aspect, the invention relates to a method of collecting optical coherence data and spectroscopic data from a sample. In one embodiment, the method includes the steps of transmitting light in a first material having a first index of refraction to the sample; receiving the light from the sample; transmitting scattered light from the sample having a first mode in the first material having a first index of refraction to a first detector, transmitting scattered light from the sample having a second mode in a second material having a second index of refraction to a second detector; and generating an optical coherence tomography image of the sample having spectroscopic data overlaid thereon. In another embodiment of the method, the scattered light having a first mode and the scattered light having a second mode are transmitted coaxially in a fiber core and a first cladding layer, respectively. In yet another embodiment of the method, the step of transmitting light in a first material having a first index of refraction to the sample further comprises the step of rotating the first material.

In one embodiment of the method, the scattered light having a second mode is transmitted in a first cladding layer. In another embodiment, the method further includes the step of terminating a second cladding layer such that the scattered light having a second mode exits the first cladding layer at an angle before reaching the second detector. In another embodiment, the optical coherence tomography image is a 3-D image and the spectroscopy data is a color representation of the sample. In yet another embodiment, the method further includes the step of calibrating for collection efficiency such that the optical coherence tomography image is in focus.

In yet another aspect, the invention relates to a method of collecting optical coherence data and spectroscopic data from a sample. In one embodiment, the method includes the steps of transmitting optical coherence tomography light through an optical fiber to the sample; receiving the optical coherence tomography light from the sample; transmitting scattered optical coherence tomography light from the sample to a first detector; transmitting a first spectroscopic light having a first wavelength through an optical fiber to the sample; receiving the first spectroscopic light from the sample; transmitting the first spectroscopic light from the sample to a second detector, transmitting a second spectroscopic light having a second wavelength through an optical fiber to the sample; receiving the second spectroscopic light from the sample; transmitting the second spectroscopic light from the sample to the second detector, registering data received from the optical coherence tomography light with data received from the first and second spectroscopic lights; and generating an optical coherence tomography image of the sample having spectroscopic data overlaid thereon.

In one embodiment, the invention relates to a single clad fiber to multi-clad optical fiber connector for use in applying excitation light to a sample and obtaining reflected light from the sample. The single clad to multi-clad optical fiber connector includes a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core. The core of the dual clad optical fiber portion and the core of the single clad optical fiber portion have substantially similar indices of refraction. The excitation light is propagated by core of the dual clad optical fiber, and light reflected by the sample is propagated by the first cladding layer of the dual clad optical fiber portion.

In one embodiment, the invention relates to a method for providing excitation light to a sample and separating received reflected light from the sample and includes the steps of: providing a single clad to multi-clad optical fiber connector that includes a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core, wherein the core of the dual clad optical fiber portion and the core of the single clad optical fiber portion have substantially similar indices of refraction, and applying excitation light to the core of the dual clad optical fiber, and extracting light reflected by the sample and propagated by the first cladding layer of the dual clad optical fiber portion.

In one embodiment, the invention relates to an optical system that includes a single clad to multi-clad optical fiber connector that includes a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core, the single clad optical fiber portion for optical communication with a light source; wherein the core of the dual clad optical fiber portion and the core of the single clad optical fiber portion have substantially similar indices of refraction; and a probe in optical communication with the dual clad optical fiber portion, wherein excitation light is propagated by core of the dual clad optical fiber, and wherein light reflected by the sample is propagated by the first cladding layer of the dual clad optical fiber portion.

Another aspect of the invention is a method for providing excitation light to a probe and separating received reflected light from the probe. In one embodiment, the method includes the steps of providing a single clad to multi-clad optical fiber connector including a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core. The core of the dual clad optical fiber portion and the core of the single clad optical fiber portion have substantially similar indices of refraction, and applying excitation light to the core of the dual clad optical fiber, and extracting light received from the probe and propagated by the first cladding layer of the dual clad optical fiber portion.

In another aspect, the invention relates to an optical system including an optical light source; a single clad to multi-clad optical fiber connector comprising: a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core, the single clad optical fiber portion for optical communication with the optical light source; wherein the core of the dual clad optical fiber portion and the core of the single clad optical fiber portion have substantially similar indices of refraction; and a probe in optical communication with the dual clad optical fiber portion, wherein excitation light is propagated by core of the dual clad optical fiber, and wherein light reflected by the sample is propagated by the first cladding layer of the dual clad optical fiber portion; and a detector in optical communication with the single clad to multi-clad optical fiber connector, wherein the detector detects light reflected by the sample and ejected by the first cladding layer of the dual clad optical fiber portion.

In another embodiment, the optical system includes an optical coupler for coupling light from the optical light source into the core of the single clad optical fiber portion. In another embodiment, the optical system includes a rotatable optical coupler in the optical path between the optical coupler for coupling light from the optical light source into the core of the single clad optical fiber portion and the probe. In one embodiment, the rotatable optical coupler in the optical path between the optical coupler for coupling light from the optical light source into the core of the single clad optical fiber portion and the probe is positioned adjacent the optical coupler. In one embodiment, the rotatable optical coupler in the optical path between the optical coupler for coupling light from the optical light source into the core of the single clad optical fiber portion and the probe is positioned within the optical path defined by the single clad fiber. In one embodiment, the rotatable optical coupler in the optical path between the optical coupler for coupling light from the optical light source into the core of the single clad optical fiber portion and the probe is positioned within the optical path defined by the double clad fiber. In one embodiment, the rotatable optical coupler in the optical path between the optical coupler for coupling light from the optical light source into the core of the single clad optical fiber portion and the probe is a part of the single clad to multi-clad optical fiber connector.

In one aspect, the invention relates to a method for obtaining information about a sample that includes providing a single clad to multi-clad optical fiber connector comprising a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core: and a single clad optical fiber portion in optical communication with the dual clad optical fiber portion, the single clad optical fiber portion comprising a core and a first cladding layer adjacent the core, wherein the core of the dual clad optical fiber portion and the core of the single clad optical fiber portion have substantially similar indices of refraction; and providing a probe in optical communication with the dual clad optical fiber portion and in optical communication with the sample, applying excitation light to the single clad optical fiber portion; wherein excitation light is propagated by core of the dual clad optical fiber, and wherein light reflected by the sample is propagated by the first cladding layer of the dual clad optical fiber portion; and detecting light reflected by the sample and ejected by the first cladding layer of the dual clad optical fiber portion. In one embodiment, the method includes the step of rotating the probe. In another embodiment, the method further includes the step of rotating the single clad to multi-clad optical fiber connector.

In one aspect, the invention relates to an optical imaging system. In one embodiment, the system includes an optical light source; a single clad to multi-clad optical fiber connector comprising a dual clad optical fiber portion, the dual clad optical fiber portion comprising a core, a first cladding layer adjacent the core, and a second cladding layer adjacent the first cladding layer, the first cladding layer and the second cladding layer having lower refractive indices than the core; and a single clad optical fiber portion in optical communication with the dual clad optical fiber portion, the single clad optical fiber portion comprising a core and a first cladding layer adjacent the core, the single clad optical fiber portion for optical communication with the optical light source; wherein the core of the dual clad optical fiber portion and the core of the single clad optical fiber portion have substantially similar indices of refraction; and a probe in optical communication with the dual clad optical fiber portion, wherein excitation light is propagated by core of the dual clad optical fiber, and wherein light reflected by the sample is propagated by the first cladding layer of the dual clad optical fiber portion; a detector in optical communication with the single clad to multi-clad optical fiber connector, wherein the detector detects light reflected by the sample and ejected by the first cladding layer of the dual clad optical fiber portion; an OCT module; and a beam splitter/combiner, the beam splitter/combiner in the optical path between the light source and the probe and in the optical path between the OCT module and the probe; wherein light from the OCT module and light from the light source are combined prior to being transmitted to the probe. In another embodiment the system further includes a rotatable optical coupler in the optical path between the optical light source and the probe and wherein the probe rotates.

In another aspect, the invention relates to a method for generating an optical image. In one embodiment the method includes providing a probe in optical communication with the dual clad optical fiber portion and in optical communication with the sample, applying excitation light to the single clad optical fiber portion; wherein excitation light is propagated by core of the dual clad optical fiber, and wherein light reflected by the sample is propagated by the first cladding layer of the dual clad optical fiber portion; providing an OCT module in optical communication with the probe; providing a beam splitter/combiner, the beam splitter/combiner in the optical path between the light source and the probe and in the optical path between the OCT module and the probe; combining light from the OCT module and light from the light source prior to being transmitted to the probe and detecting light reflected by the sample and ejected by the first cladding layer of the dual clad optical fiber portion. In another embodiment, the method further includes the step of rotating the probe. In still another embodiment, the method further includes the step of constructing an OCT image from the light reflected by the sample. In yet another embodiment, the method further includes the step of analyzing light reflected by the sample and ejected by the first cladding layer and overlaying the analyzed light on the OCT image. In one embodiment of the method, the OCT image is a 3-D image and the analyzed light is a color overlay on the 3-D image.

The devices, systems and methods are explained through the following description, drawings, and claims.

BRIEF DESCRIPTION OF THE DRAWINGS

The patent or application file contains at least one drawing executed in color. Copies of this patent or patent application publication with color drawings will be provided by the Office upon request and payment of the necessary fee.

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views. The drawings associated with the disclosure are addressed on an individual basis within the disclosure as they are introduced.

FIG. 1A is a schematic diagram of an illustrative embodiment of a coupler suitable for imaging with a single-fiber probe constructed in accordance with the invention.

FIG. 1B is a schematic diagram showing a cross section of an illustrative embodiment of a single clad fiber in accordance with the invention.

FIG. 1C is a schematic diagram showing a cross section of an illustrative embodiment of a multiple clad fiber in accordance with the invention.

DETAILED DESCRIPTION

Figure 2:
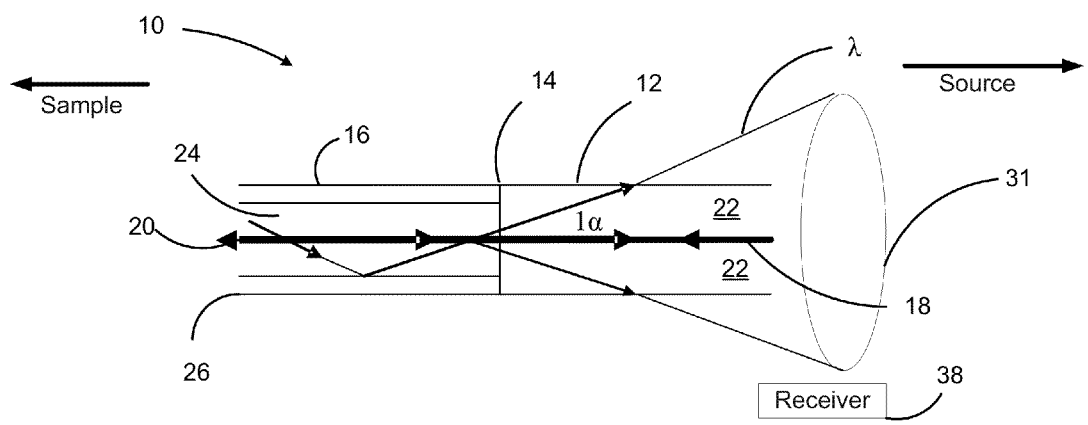
FIG. 2 is a schematic diagram of a cladding coupler constructed in accordance with an illustrative embodiment of the invention.

FIG. 1A shows an exemplary optical coupler 10, constructed in accordance with an illustrative embodiment of the invention. A single-clad fiber (SCF) 12 is optically coupled to a dual-clad fiber (DCF) 16. In some embodiments, excitation light injected into the core 18 of SCF 12, enters the core 20 of DCF 16, and then propagates to a rotating imaging probe at the other end of the DCF 16 (not shown). FIG. 1B shows a cross-sectional view of the SCF 12 of FIG. 1A. SCF 12 has a core 18 and a single cladding layer 22. FIG. 1C shows a cross-sectional view of the DCF 16 of FIG. 1A. DCF has a core 20, a first (or inner) cladding layer 24, a second (or outer) cladding layer 26 and a jacket 27. Typically, the diameter of the outer cladding 26 matches the diameter of the cladding 22 in the SCF because most fibers are the same size. However, variations in fiber sizes and custom fibers are possible such that the diameters of coupled fibers or cladding layers can differ.

FIG. 2 shows further details of an embodiment of a DCF coupler 10 constructed in accordance with an illustrative embodiment of the invention. The coupler 10 is used to facilitate imaging a sample (left side, not shown) and detecting the return light at a detector (right side, not shown). In this embodiment, a DCF fiber 16 is connected to a matching SCF 12 that does not have a second, outer cladding layer 27. The SCF 12 otherwise has similar geometry, core composition, and cladding as the DCF 16. In one embodiment one end of the matched SCF 12 is surrounded by index-matching material and is coupled to an applicable optical apparatus to inject or collect light, while the other end of the matched SCF 12 is optically connected at interface 14 to the DCF 16. The connection 14 between the DCF 16 and the matching SCF 12 can be achieved by, for example, fusion splicing or by butt-coupling.

With continued reference to FIG. 2, the DCF 16 has a core 20, an inner cladding layer 24 and an outer cladding layer 26. The goal of the configuration is to couple light into and out of the inner cladding 24 of the DCF. The core 18 of the SCF 12 is matched to the core 20 of the DCF 16 in both diameter and refractive index, and the SCF cladding 22 is matched to the inner cladding 24 of the DCF 16 in refractive index.

Considering the example of coupling light out of the inner cladding of the DCF; excitation light is injected from a light source (not shown—right side of the figure) into core 18 of SCF 12 and enters core 20 of DCF 16 via coupling interface 14. Excitation light then propagates down core 20 to a probe at the end of DCF 16 where the excitation light exits the probe and impinges on a sample. Subsequently, light (λ) reflected by the sample is collected by the probe and is guided in the inner cladding 24 of DCF 16 because the outer cladding 26 layer has lower refractive index than the inner cladding layer 24. Some reflected light also enters the core 20 of DCF 16. At the interface 14 between the DCF fiber 16 and the SCF 12, because the refractive indices are well matched, both the light in the core 20 and in the inner cladding 24 of the DCF propagate into the core 18 and the cladding 22 of the SCF without significant interface reflection and intensity loss.

Reflected light in the inner cladding 24 of DCF 16 is guided into the cladding 22 of the SCF 12. Because the SCF 12 does not have an outer cladding layer, light can be readily guided out of the cladding 22 by surrounding the SCF 12 with a higher index media such that the light is no longer guided along the fiber. The shape of such light propagation is a cone structure 31 whose angle α is determined by the relative refractive indices of the cladding layer and the media. One of the regions from which the light cone exits the outer surface of the fiber is an emission region. A detector can be placed near such as region to collect a spectroscopic signal. To the extent a jacket or other coating is applied to a portion of the outer surface of the fiber segment where the cone would otherwise form, the region for coupling light out of the fiber, such as the emission region, can be specified and controlled. The light cone escaping from the SFC 12 can be captured by a detector directly in its path or redirected by optical apparatus. The same principle can be extended to arbitrary cladding geometries.

Figure 3A:
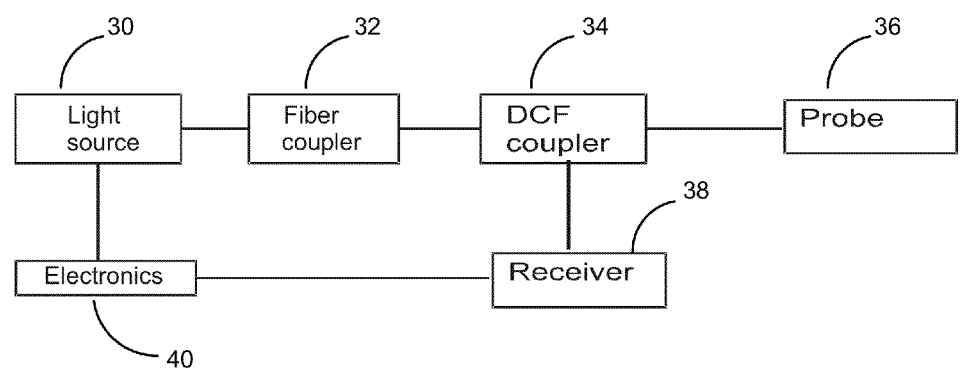
FIG. 3A is a block diagram of an imaging system constructed in accordance with an illustrative embodiment of the invention.

FIG. 3A is a block diagram showing the basic components of an imaging system constructed in accordance with an embodiment of the invention. The imaging system includes a light source 30, a fiber coupler 32 (e.g., a mirror, lens, or prism assembly), a DCF coupler 34, a sample imaging probe 36, an optical receiver 38, and electronics 40 for generating control signal and data recording. The system can include a single-core fiber (e.g., a SCF) which carries injected light from the light source 30 to the DCF coupler 34. The probe 36 can be forward scanning, side scanning or other suitable configurations.

Figure 3B:
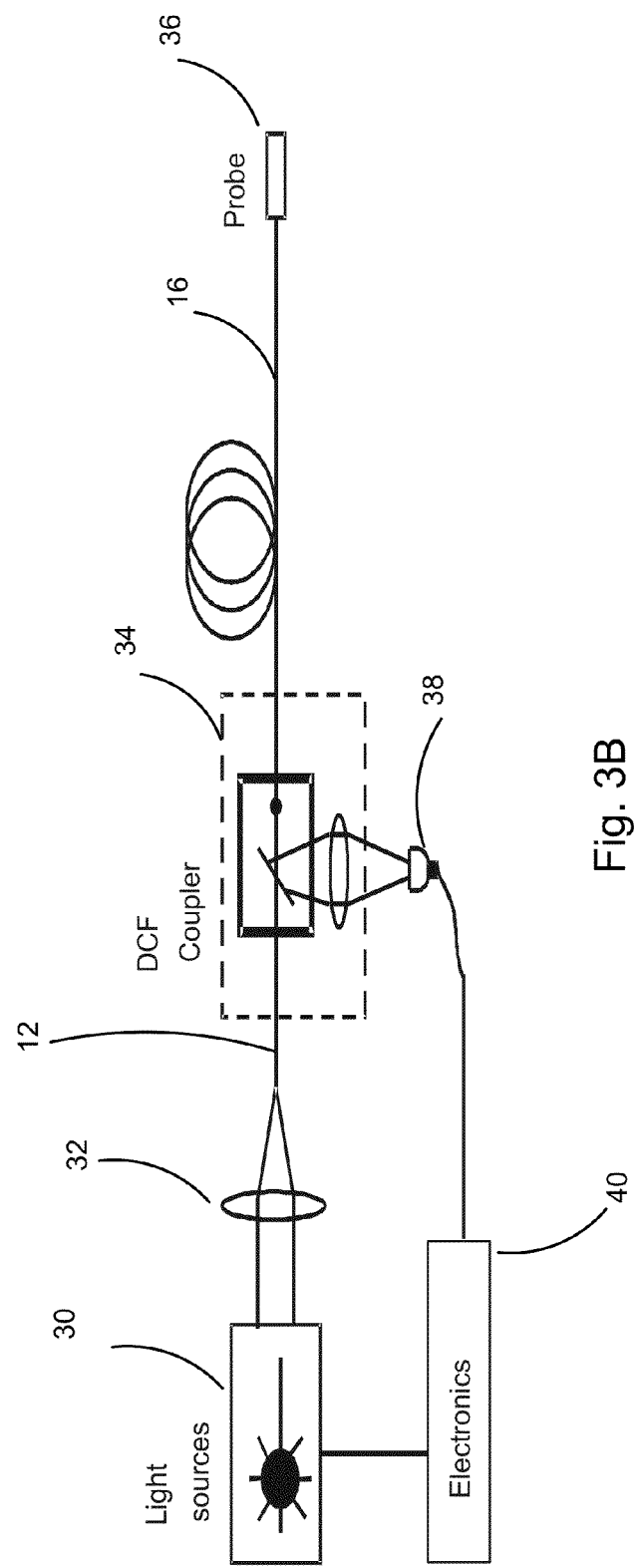
FIG. 3B is a schematic diagram of an imaging system in accordance with an illustrative embodiment of the invention.

Referring to FIG. 3B, in one embodiment a light source 30 is coupled to the core of a single-core fiber (e.g., a SCF) 12 by a fiber coupler 32. This excitation light from the source 30 is injected through a fiber coupler 32 and into the core 18 (FIG. 1) of the single-core fiber 12, passes through DCF coupler 34, and continues propagating in the inner core 20 of DCF 16 until it exits the fiber through the probe 36 and propagates to the sample. Some light is reflected by the sample and this reflected light is collected by the probe 36 and transmitted to both the inner cladding 24 and the core 20 of the DCF (FIG. 1). Because the diameter and the numerical aperture of the inner cladding 24 are larger than those of the core 20, more light is collected by the inner cladding 24 than by the core 20. The light that is collected by the inner cladding 24 propagates along the inner cladding 24 of the DCF 16 back to the DCF coupler 34, where the light is coupled out of the fiber to another fiber or directly to an optical receiver 38, such as an optical detector or a spectrometer. The optical receiver can include photodiode-based detectors or other components suitable for converting an optical signal to an electric signal.

In one embodiment, a single detector can be used in the optical receiver 38 to collect light propagating along or within the light field designated by cone 31 in FIG. 2 or as otherwise shown by the coupler 34. The optical receiver 38 can be used to capture serially generated signals associated with different colors or wavelengths of light. Alternatively, a demultiplexer or other device can be used to collect a plurality of wavelengths or colors in parallel and direct the demultiplexed beams to multiple detectors at the optical receiver 38 such that each detector is used to capture each of the plurality of wavelengths or colors propagated through cladding 22. However, sequential processing of signals containing color information on one detector is preferred as a result of the cost savings and reduced complexity associated with not having to deal with parallel signals and the demultiplexing of the same.

As shown in FIG. 3B, electronic circuits 40 are used to control and supply power to the light source, the optical receiver, etc. Additional electronics and computers can be added to for further control signals, coordinating probe movement, data processing and displaying. A demultiplexer and a detector array used in receiver 38 can also be in electronic communication with suitable control and power circuits 40.

In one embodiment, the light source can include, without limitation, a broadband light source such as superluminescent white light sources, supercontinuum generation light sources, black-body radiation light sources, light emitting diodes (LED), laser-pumped phosphors, superluminescent light emitting diodes (SLED), or broadband lasers such as $Ti:Al_2O_3$ lasers.

In one embodiment, light from a given source is coupled into the single-core fiber and propagates there through with a level of intensity suitable for propagating to and from a sample such that a composite image can be generated. For this, high-irradiance light sources with suitable emission angles, such as the lasers or SLEDs, are preferred over the other sources such as blackbody radiation, LEDs, or phosphor light sources. In another embodiment, the light sources may be constructed of an assembly of light sources of different wavelengths. Although the individual light sources may be either broad or narrow band, the assembly is designed to cover a spectral band of interest. For example, a white light source can be made by combining three narrowband lasers that emit red, green and blue light. The light of different wavelengths can be combined by dichroic mirrors or by prisms. To achieve the desired imaging results, the light sources are selected and configured to provide a suitable contrast level for each application. In addition, it may be desirable to use multiple light sources simultaneously, depending on the imaging application.

In one embodiment, the light sources are chosen to generate images that resemble the images seen by human eye in a relatively natural setting. To achieve this, broadband white light sources with spectrum coverage within the visible light spectra (380-750 nm) are chosen. Examples of such light sources include white superluminescent sources, supercontinuum generation sources, blackbody radiation sources, white LEDs, and fluorescence light sources. In addition, because human eyes have three types of color-sensing retinal cells, each responding to red, green, and blue colors, an assembly of narrowband light sources can be combined to achieve the same effect. For example, three lasers with individual outputs that span most of the visible spectrum (e.g., laser 1 in the 580-750 nm band, laser 2 in the 495-580 nm band and laser 3 in the 380-495 nm band), can be combined by dichroic mirrors to generate white light.

In another embodiment, the light sources are chosen to generate a tailored level of contrast for a particular disease signature, structural feature, or chemical compositions. For example, because hemoglobin in the red blood cell has a sharp transition of optical absorption around 580-620 nm, a light source or an assembly of light sources that spans this range offers high sensitivity for thrombus detection in blood vessel imaging. In another example, because the cholesterol and cholesterol esters have an absorption signature in the infrared spectrum around 1680-1720 nm, light sources spanning that range offer high sensitivity for the detection of lipid plaques during blood vessel imaging.

Figure 4A:
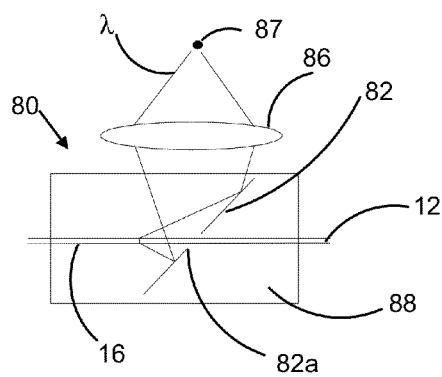
FIGS. 4A-D are schematic diagrams of exemplary optical arrangements for guiding light from a fiber to another light guide or to a detector constructed in accordance with illustrative embodiments of the invention.

In another embodiment, a DCF coupler includes a device configured to maintain the continuity of the light propagation from the core of the single-core fiber to the core of the DCF, while allowing the light at the inner cladding of DCF to be coupled out. An optical apparatus can be incorporated to aid in collection of reflected light or ejection of excitation light in the DCF coupler 34. FIG. 4A shows an embodiment of such an optical apparatus 80.

As shown, a mirror 82 with a central hole 82a allows the fiber 12 to pass through but reflects most of light (λ) escaping the cladding of fiber 16 in a direction substantially perpendicular to the fiber 16. The light escaping the fiber has a conical profile as previously discussed with respect to FIG. 2. In one embodiment, a lens assembly 86 is used to focus the light to a small aperture for collection or measurement. If the refractive index matching media 88 surrounding the fibers 12 and 16 is a liquid, the fibers 12 and 16 can be either stationary or rotating. If the fibers are rotating, as long as the mirror 82 does not rotate, the light λ is guided to a stationary point 87.

Figure 4B:
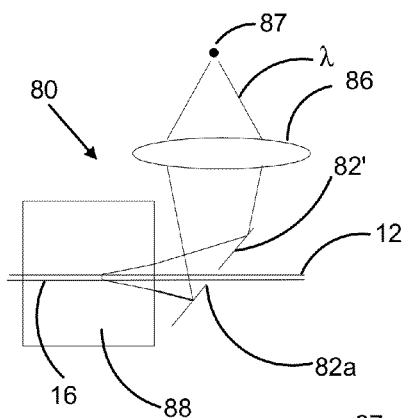
Figure 4C:
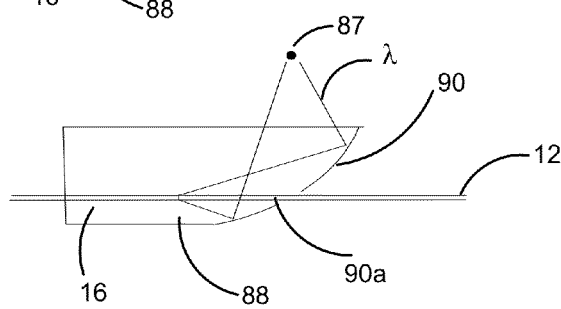

FIG. 4B shows a similar embodiment except the mirror 82' is moved out of the matching refractive index matching media 88 for ease of manufacturing. FIG. 4B also permits fiber rotation even if the media is solid or is confined inside a solid rotating container. In the embodiments of both FIGS. 4A and 4B, the flat mirror 82 can be replaced with a curved mirror (not shown) to aid in light focusing and collection. FIG. 4C shows another embodiment in which the surrounding refractive index matching media 88 is shaped such that the light is reflected and focused by the shaped reflecting surface 90.

Figure 4D:
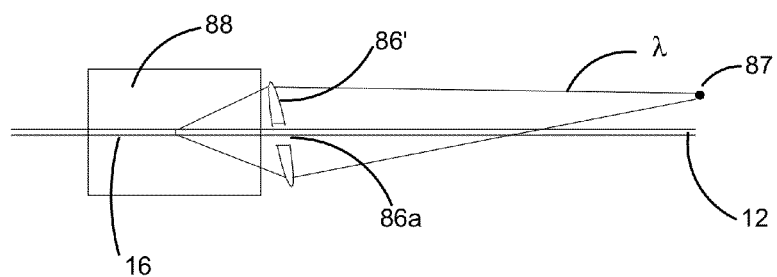

FIG. 4D shows another embodiment in which a lens assembly 86' has a hole 86a that allows the fiber 12 to pass through but the out-coupled light (λ) is redirected by the lens assembly. The optic elements and assemblies mentioned herein can also be embedded in or molded in place with the surrounding refractive index matching media rather than being standalone. To improve optical and mechanical properties of the device, anti-reflective coatings and other performance-enhancing coating may be applied to interfaces. It should be noted that FIGS. 4A-D only show examples of optical arrangement. Other configurations are possible without departing from the scope and spirit of the invention.

The distal part of the miniature probe provides optics for both launching light into the sample and collecting reflected light from the sample. It typically includes a refractive lens or a GRIN lens and may contain a scanning mechanism. Other configurations are also possible, such as those based on shaped reflectors or shaped lens. Because the core of a DCF has smaller diameter and often has a smaller numerical aperture than the inner cladding, back reflected light from the core is collected by the inner cladding, resulting in potential crosstalk. Therefore, the optical path is configured to minimize back reflection.

Figure 5:
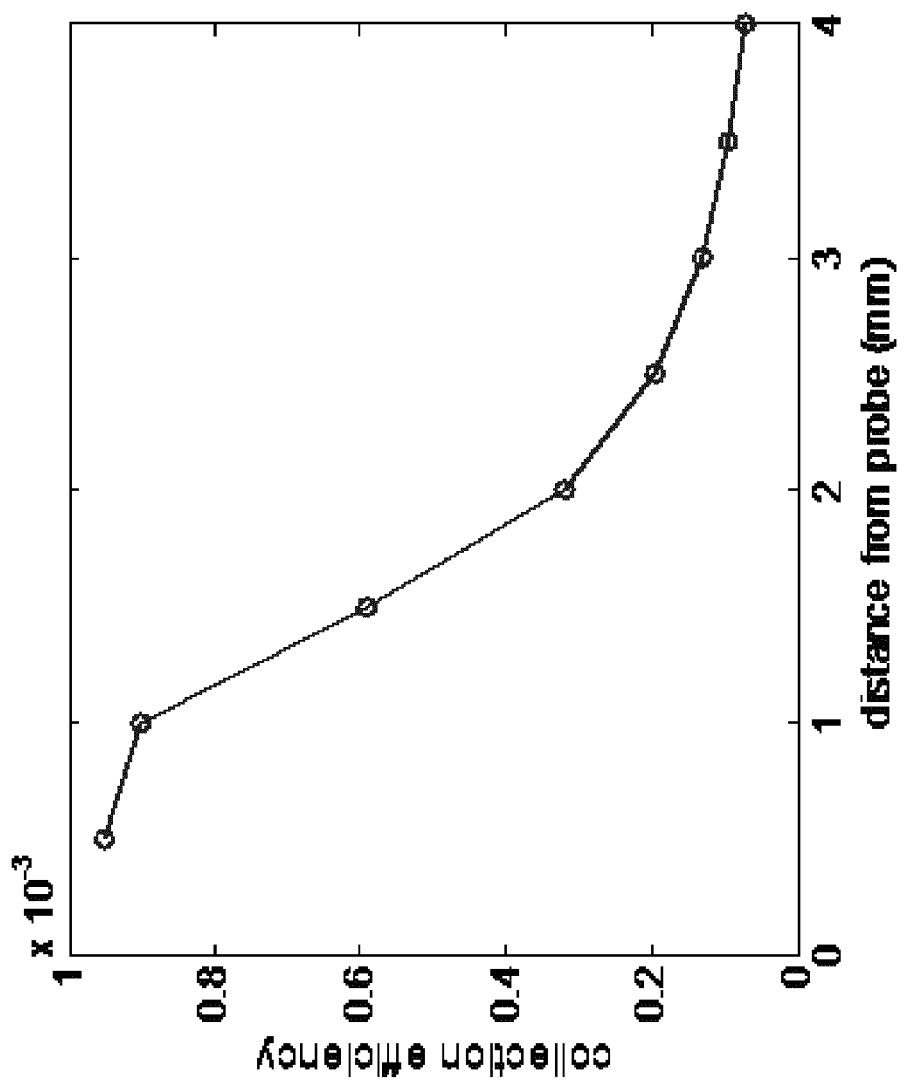
FIG. 5 is a graph showing measurement of collection efficiency as a function of sample distance to the probe of a light source through an embodiment of the system constructed in accordance with the invention.

When the incident light interacts with the sample, it can undergo various optical processes that include absorption, scattering, reflection, fluorescence, and non-linear interactions. Once scattered from the sample, such as an artery, a portion of modified light propagates back and is collected by the aperture of the probe. The collection efficiency associated with this portion of light is a complex function of the numerical aperture (NA) of the DCF core, the NA of the DCF inner cladding, and the properties of the lens. FIG. 5 shows the collection efficiency of 532 nm light delivered and collected by an imaging probe and associated data processing system that includes a white diffuse reflection standard.

When the light collected from the sample propagates back along the inner cladding and reaches the DCF coupler, the light is coupled out (i.e., out-coupled) of the cladding. In one embodiment, out-coupled light is first separated by prism or gratings, or by a set of dichroic or absorption filters (not shown). After the separation, the intensities of light of different wavelengths are measured by optical detectors. This demultiplexing process is used when non-OCT light, i.e., the light used for color information, is delivered to a sample simultaneously such that multiple colors of light arrive in parallel. The measurement of each detector represents the intensity of the light in a particular wavelength range. In another embodiment, the out-coupled light is measured by a spectrometer. In yet another embodiment, the out-coupled light is detected by one optical receiver, but the lights of different wavelengths are encoded either by frequency-division multiplexing or time-division multiplexing.

Alternatively, the out-coupled light can include one wavelength of light that is transmitted along the inner cladding while the probe is stationary, moving or otherwise rotating. Several different wavelengths of light can be sent and received along the inner cladding to reach the sample and return for processing before the spin rate of the optical fiber causes it to translate to a new spatial position of the sample.

In addition, the multiplexing arrangement can be enhanced if the excitation light source is made of an assembly of light sources of different wavelengths. In frequency-division multiplexing, the light sources of different wavelength are encoded with different modulation frequencies. In time-division multiplexing, the light sources of different wavelengths are turned on at different time intervals and electronic decoders are used to separate the signals from the different wavelengths.

Figure 6:
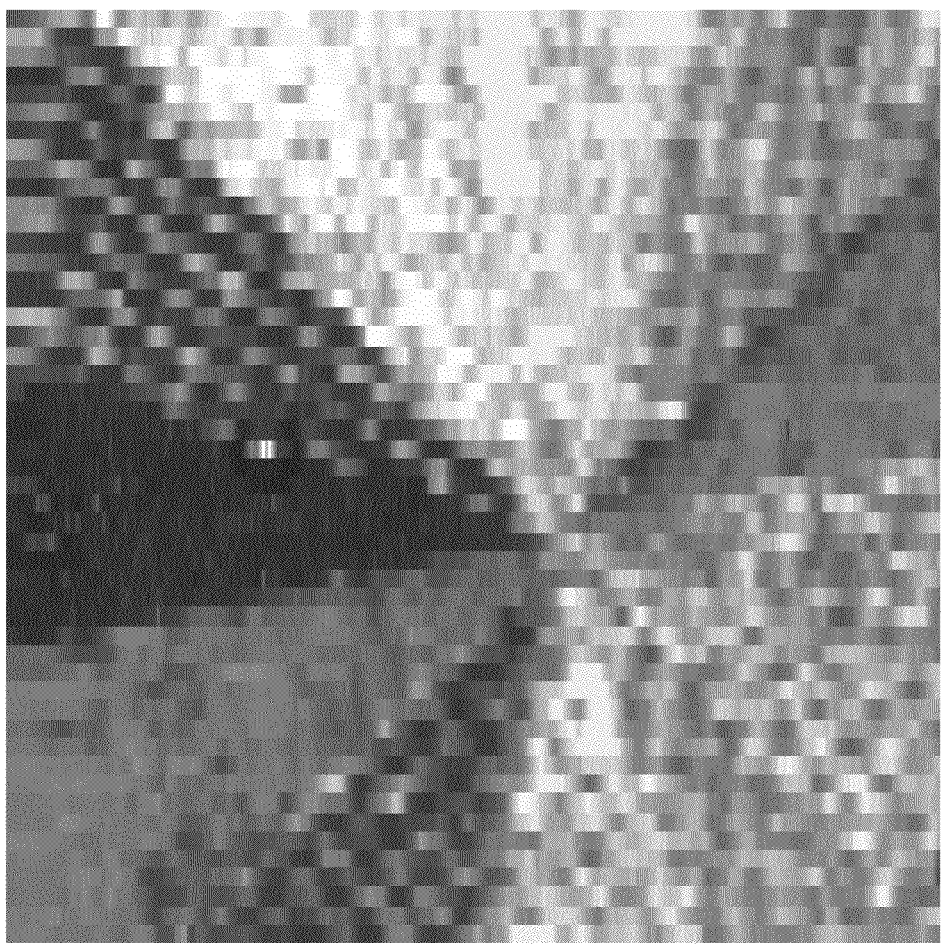
FIG. 6 shows an exemplary color image of a color wheel pattern printed on a white paper, obtained by a system and probe built in accordance with an illustrative embodiment of the invention.

To obtain a visual image, either the probe head or the sample can be translated in a raster motion to collect 2D or 3D information. Such scanning mechanisms are similar to those widely used for other applications such as confocal microscopy or OCT. FIG. 6 shows an example image of a color wheel pattern printed on a white paper, which was obtained by raster-scanning the probe in FIG. 3A across the sample. The colors are resolved accurately and with high spatial resolution.

For some types of samples, such as blood vessels or the gastro-intestinal (GI) tract, the spiral scanning is preferred and more efficient than raster scanning. In order to achieve this, an optical rotational joint is used to connect the optical fiber to the light source. FIGS. 7A-7D show four respective embodiments of a rotary joint. These embodiments are suitable for implementing spiral scanning according to an embodiment invention. The rotary joint can be located at the fiber coupler 32, at the single-core fiber 12, at the DCF coupler 34, or at the DCF 16; each arrangement has advantages for specific applications.

Figure 7A:
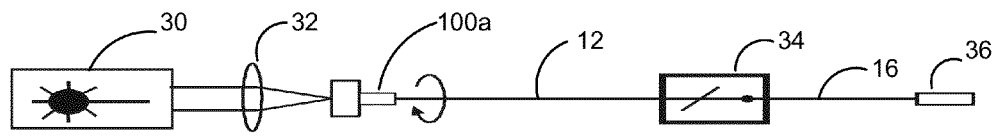
FIGS. 7 A-D are schematic diagrams of different embodiments of a rotatable device for obtaining images from a rotating probe in accordance with an illustrative embodiment of the invention.

Considering FIG. 7A, when the rotary joint 100a is located at the fiber coupler 32, the rotary joint 100a transfers light from the sources directly to a single-core fiber 12 without intervening fiber optics. This arrangement simplifies the optical design of the rotary joint 100a and mitigates cross talk because the cladding light in the single-core fiber is not guided. No excitation light propagates in the cladding. Instead, some light from sample is transmitted back in the cladding. Thus, the light in the core, or such scattered light configured for use by an OCT system, is collected once scattered from the system and light returning from the sample configured to generate color information for the sample is collected in the cladding.

However, because the DCF coupler 34 rotates in this case, a special design is required to ensure that the DCF coupler maintains coupling efficiency and mechanical integrity during rotation. If the light source is broadband, it is often difficult to design a single lens that focuses all the wavelengths efficiently into a single rotating fiber. Thus, it sometimes is advantageous to divide the light into several wavelength bands using dichroic mirrors or prisms (not shown), and to add optics to adjust the optical focusing of different wavelength bands individually. This is especially useful if the light source is made of an assembly of multiple narrowband sources.

Figure 8:
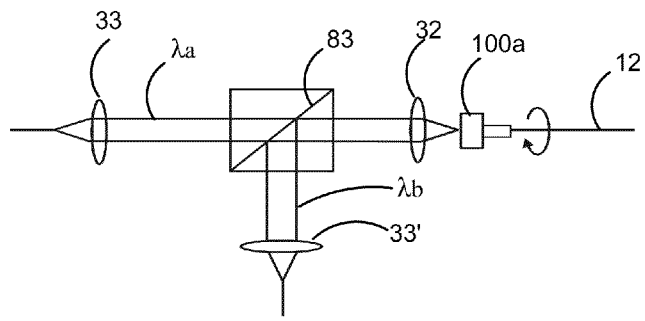
FIG. 8 is a schematic diagram of an embodiment of a device for combining two wavelength bands to improve throughput in accordance with an illustrative embodiment of the invention.

FIG. 8 shows an embodiment of such a device for two wavelength bands λa, λb from two different sources with lenses 33, 33' combined by a dichroic mirror 83 prior to being refocused by lens 32 injected into the core of SCF 12 through rotary joint 100a.

Figure 7B:
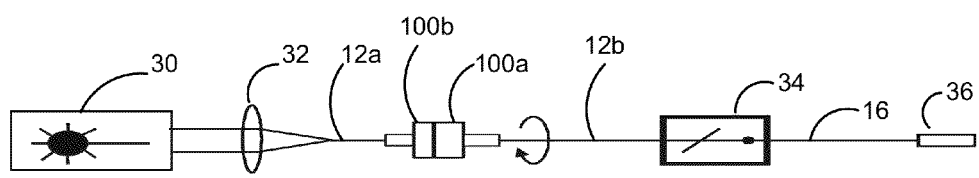

Referring to FIG. 7B, when the rotary joint 100a, b is located at the single-core fiber, the rotary joint 100a, 100b transfers light from one single-core fiber 12a to another single-core fiber 12b. Because the single-core fibers are used widely, many off-the-shelf rotary joints can be used for this purpose. Further, since the cladding light is not guided, crosstalk of core and cladding light is reduced across the joint.

Figure 7C:
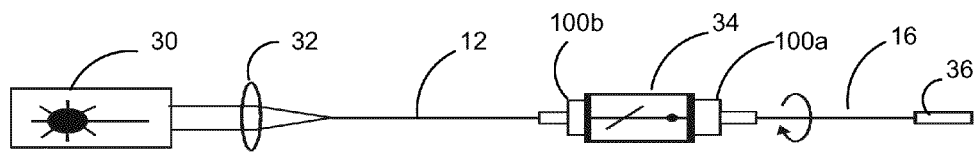

Referring to FIG. 7C, when the rotary joint 100a, 100b is located at the DCF coupler 34, the rotary joint transfers the light from the core of the single-core fiber 12 to the core of the DCF 16, and collects the light from the inner cladding of DCF to another multi-mode fiber or directly to the optical receiver. This configuration reduces possible optical interfaces, saves space and increases the light coupling efficiency.

Figure 9:
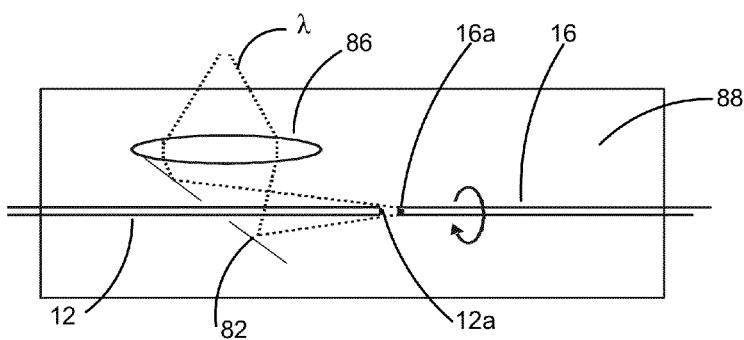
FIG. 9 is a schematic diagram showing an embodiment of a device that acts both as a rotary joint and as a DCF coupler constructed in accordance with an illustrative embodiment of the invention.

Referring momentarily to FIG. 9, an optical arrangement is shown that couples light from the cladding of a rotating DCF. The single-core fiber 12 is on the left side and the DCF 16 is on the right side. This is similar to what is shown for FIG. 4A, but a rotating fiber and with the lens 86 being located in a refractive index matching medium 88. The fiber ends are cleaved and submerged in an index matching fluid 88 with a refractive index matched to the cladding of the single-core fiber 12.

In one embodiment, the two fibers are placed in close proximity such that the fiber ends 12a, 16a are within confocal distance of each other. With this configuration, there is strong coupling between the core of the single-core fiber 12 and the DCF 16 such that most optical power from the single-core fiber transmits to the core of the DCF. However, because the surrounding media 88 is refractive matched to the cladding of the single-core fiber, the light exiting from the inner cladding of the DCF passes unguided and unobstructed into the surrounding media. This light can be either be detected directly by detectors or redirected by optics such as a mirror 82 and lens 86 toward a detector or another fiber.

Figure 7D:
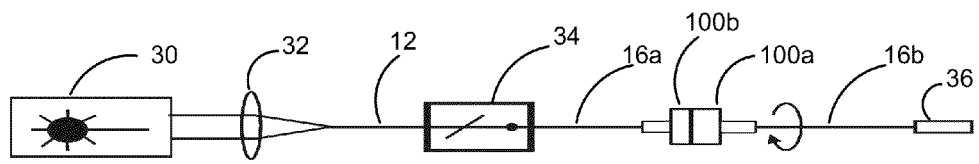

Referring to the FIG. 7, FIG. 7D depicts an embodiment in which the rotary joint 100a, 100b is located at the DCF 16, the rotary joint 100a, 100b transfers light from the core and the inner cladding of one fiber portion DCF 16a to the core and the inner cladding of the other fiber portion DCF 16b, respectively. In this case, the DCF coupler 34 is stationary and, hence, easier to manufacture. However, the rotary joint 100a, b is configured for use with a DCF fiber. In one embodiment, the joint 100a, 100b is configured to prevent light traveling in the core from propagating in the cladding such that unwanted cross-talk between the different light modes is prevented or reduced to an acceptable level.

Figure 10:
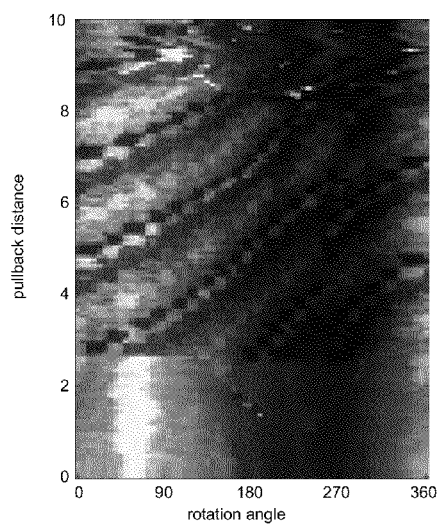
FIG. 10 shows an example of an image obtained using a rotating imaging probe having an optical fiber in accordance with an illustrative embodiment of the invention.

Once rotation of the probe is achieved, the probe is translated along the axis to acquire a spiral scan. This process of pulling back the probe along the axis allows OCT data to be collected over the length of a sample. FIG. 10 shows an example of an image reconstructed from data acquired from a spiral scan of a lumen acquired with an embodiment of the system. The sample lumen imaged in this example is rolled paper, printed with a repetitive rainbow color pattern. Because the collection efficiency is dependent on the distance from the probe to the sample and the probe is not exactly centered inside the sample, sample locations that are farther away from the probe appear darker.

Although the above methods provide color imaging, the distance from the sample to the probe cannot often be measured accurately. To achieve accurate depth imaging, the present invention provides means for combining color imaging and OCT imaging. Most of the optical components shown in FIGS. 7A-7D, including the core of the single-core fiber, the core of the DCF, the rotary joint, the DCF coupler, and the probe can be made to support the single-mode light propagation required by OCT.

Figure 11A:
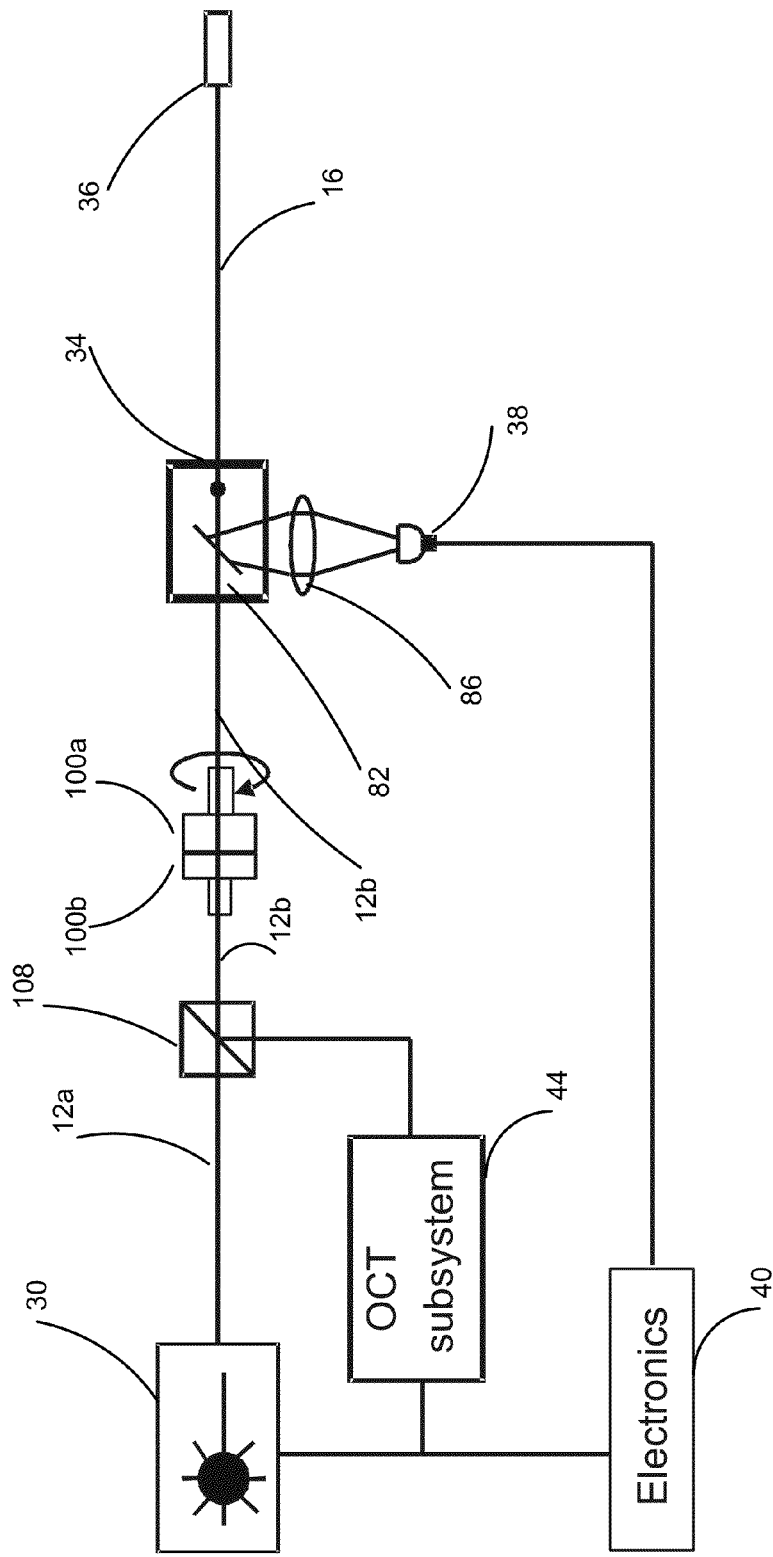
FIG. 11A is a schematic diagram of an embodiment of a system for combining spectroscopic data, such as color information, and OCT imaging data, such as distance measurements, constructed in accordance with the invention.

FIG. 11A shows a schematic of an embodiment of a combined OCT and spectroscopic system. A beam splitter/combiner 108 is used to combine the light from an OCT apparatus 44 and the light from a spectroscopic light source 30. The beam splitter/combiner 108 can be of any type that passes a sufficient fraction of light from the two input paths, including but not limited to, dichroic mirrors, fiber beam combiners, and prisms. The light then travels along the core of a fiber 12b, passing through a rotary joint 100a, 100b, a DCF coupler 34, a probe 36 and is incident onto the sample. The collected light in the DCF 16 has two parts, the light propagating along the core and that propagating along the inner cladding. At the DCF coupler 34, these two light beams separate into the two paths. A filter can be used on the exit light from the inner cladding to remove the OCT light (not shown). The light collected in the core from the sample can be compared with reference light using an interferometer to generate depth measurements, as part of the OCT subsystem. Each depth measurement or a subset of the depth measurements can be matched with a spectroscopic signal to provide color information relative to the measured position of the sample.

Alternatively, a wavelength-selective detector that it is not responsive to the OCT light can be employed to detect the reflected spectroscopic light. For the cases in which it is advantageous to use the OCT light as a wavelength component for the spectroscopic analysis, the receiver can be made to receive both the OCT light and the spectroscopic light. The light propagating along the core travels across the DCF coupler 34, the rotary joint 100a, 100b, and the beam splitter/combiner 108 to arrive back to the OCT subsystem 44. Because the spectroscopic component of the light is incoherent with respect to the OCT light, it does not generate an OCT signal.

Under other circumstances, if the spectroscopic component of the light generates background noise that degrades the signal to noise ratio of the OCT signal, a filter can be inserted into the optical path to the detector to remove it. It should be noted that although the rotary joint 100a, 100b is located between the beam splitter/combiner 108 and the DCF 34 coupler in FIG. 11A, all possible combinations and permutations of arrangements of the joints and optical elements shown implementations and are within the scope of the invention.

One embodiment of the system employing a white light source 30 for RGB imaging and an OCT subsystem 44 based on swept-source technology, such as using a swept source laser as the source for the light injected into the core and scattered from a sample, and a probe were constructed similar to the configuration shown in FIG. 11A. The OCT system used a single-mode Corning SMF-28 fiber 12. The custom-made DCF 16 had a core and inner cladding matched to the core and the cladding of the SMF-28 fiber, except the inner cladding had a diameter about 100 μm instead of 125 μm for the SMF-28 fiber. The outer cladding of the DCF had a diameter of about 125 μm. In the most distal end of the probe 36, a GRIN lens was attached to achieve optical focusing.

In addition, the probe was rotated at 10 Hz while the pullback speed was approximately 1 mm/sec. For each rotation, approximately 450 axial lines or depth measurements at different points of rotation were collected for OCT and 67 pixels were collected for spectroscopy. Although this system was designed to measure the reflectance and scattering from the inner surface of a tubular structure, it could be readily modified to detect fluorescence, two-photon, Raman, and other optic processes using the same principles. Hence, the test system constitutes an example, rather than the scope of this invention.

Figure 11B:
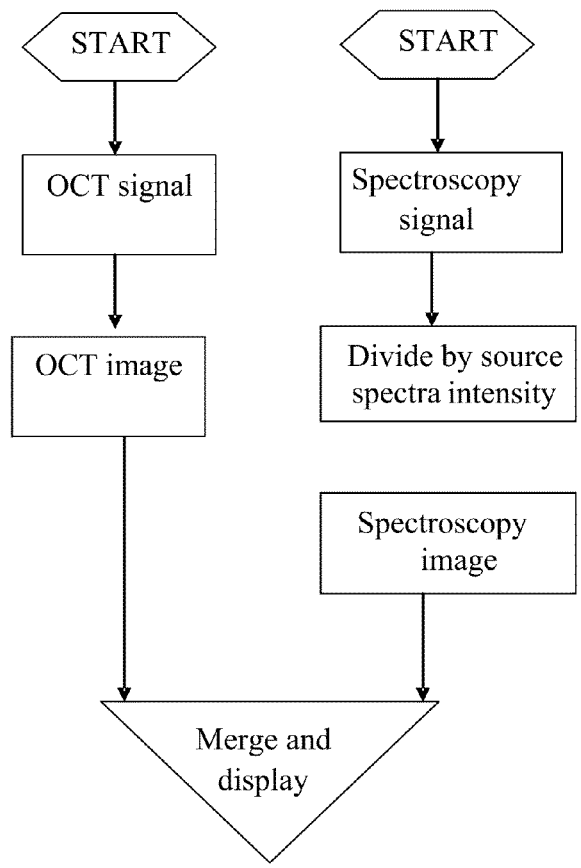
FIG. 11B is an exemplary method of generating a combined tomographic and spectroscopic dataset or image in accordance with an illustrative embodiment of the invention.
Figure 13:
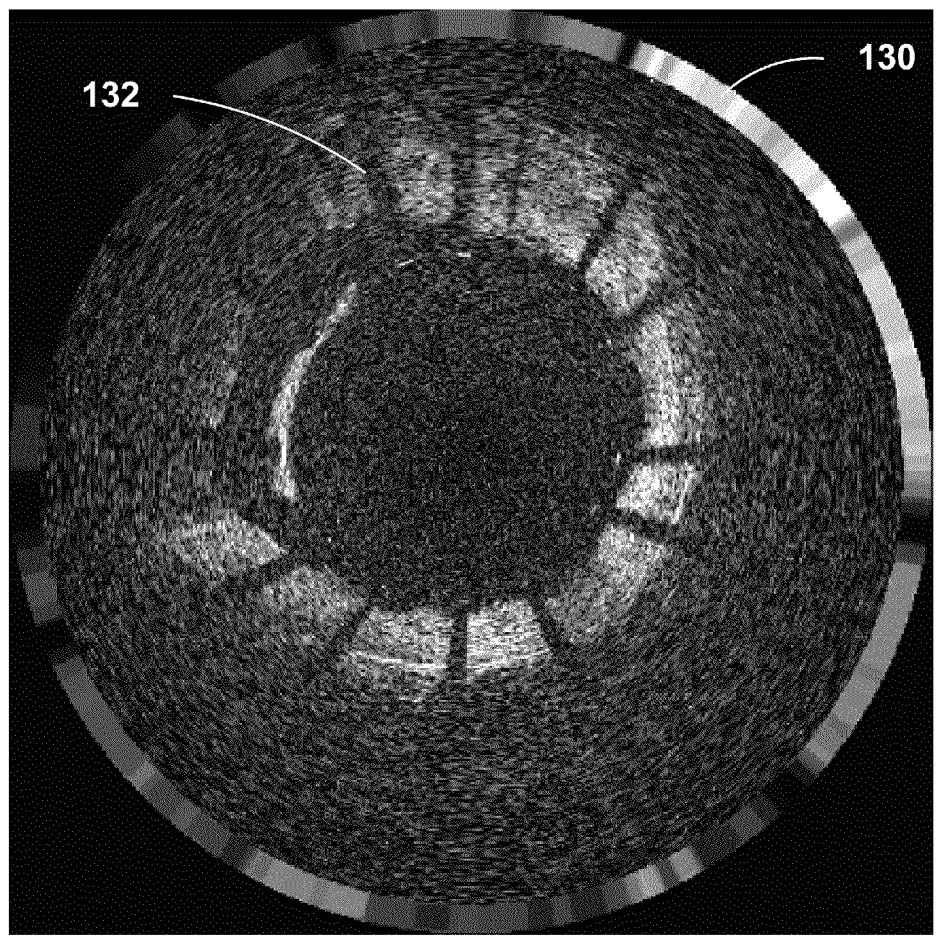
FIG. 13 shows a spectroscopic measurement superimposed on a 2D OCT image, constructed in accordance with an illustrative embodiment of the invention.

An exemplary embodiment of a method suitable for generating a combined OCT/Spectroscopy image is illustrated in FIG. 11B. As shown, the OCT and spectroscopy signals are both obtained. The OCT images are generated from the OCT signals from the fiber core using an interferometer-based subsystem such as OCT subsystem 44. The spectroscopy signal is first divided by the source spectral intensity to remove the source power variation. The resulting spectroscopy signal is then assigned a color using color mapping to generate a spectroscopy image. The spectroscopy image is overlaid on top of the OCT image to obtain the combined image. An exemplary color mapping is shown in FIG. 13 as described below.

Figure 12:
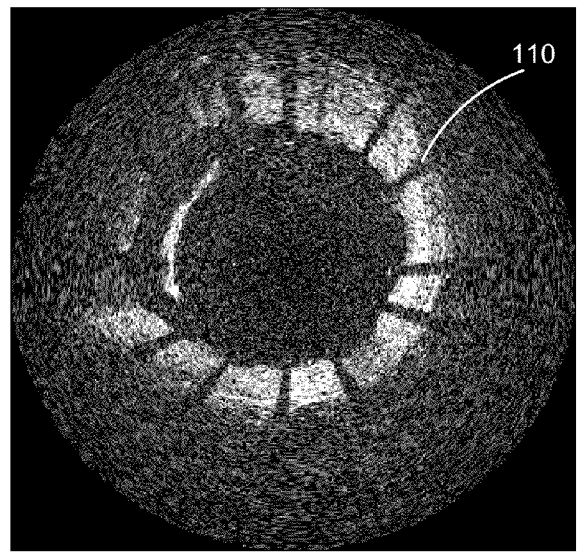
FIG. 12 shows an example of an OCT image generated using an imaging probe embodiment of the invention.

FIG. 12 shows an example OCT image of a sample obtained through the system of FIG. 11A and the combined OCT and spectroscopy probe. An explanted stented coronary artery was used as the sample. In this example, the axial and the lateral resolutions of the OCT image are preserved. The sample features, such as the artery wall structures (intima, media, advantitia), and the stent struts 110 are also preserved and are indistinguishable from images obtained by a stand-alone OCT apparatus.

Because the OCT light and the spectroscopy light share the same optical path in the probe, although coaxial in some embodiments, geometrical registration of the OCT and spectroscopic images is easily accomplished. After OCT image is obtained, the spectroscopic images 130 can be overlaid on top of OCT images 132 (FIG. 13). There are many ways by which the combination images can be displayed. FIG. 13 shows an example method to overlay the spectroscopic information in a 2D OCT cross-sectional image. The OCT image is displayed similar to those in the stand-alone OCT apparatus; the spectroscopic information can be displayed as numerical values, in full color, or in pseudo color, as a color map, around the lumen wall, the circumference, or other contours. Each cross-section of the lumen has OCT measurements that provide depth information that can be paired with color information for each scan line. By combing these cross-sections or otherwise topographically processing the data, a 3D color image of a sample can be generated.

Figure 14A:
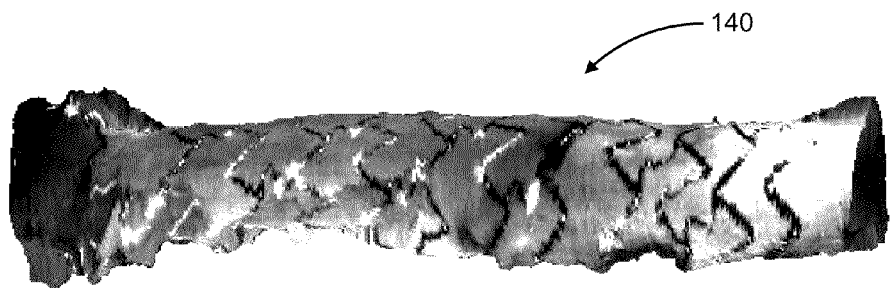
FIG. 14A shows a spectroscopic measurement superimposed on a 3D OCT image, constructed in accordance with an illustrative embodiment of the invention.
Figure 14B:
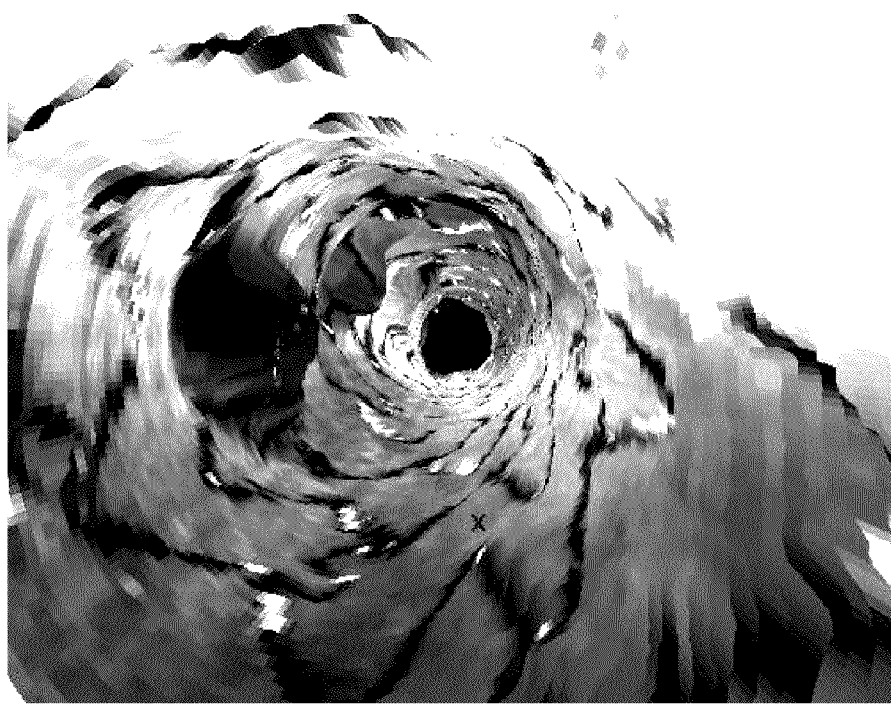
FIG. 14B shows a spectroscopic measurement superimposed on a 3D OCT image that resembles the view from a conventional forward-viewing endoscope constructed in accordance with an illustrative embodiment of the invention.

FIG. 14A shows the result of overlaying the spectroscopic information on a 3D OCT image. 3D reconstruction of the artery 140 is achieved using the 3D OCT dataset and the spectroscopy image is displayed on the lumen as colors of differing intensity. The color map can be a color surface as opposed to a color shape, such as the substantially circular color map of FIG. 13 or any real or pseudo color representation. FIG. 14B shows yet another method to overlay the spectroscopic information in a 3D OCT that resembles the view typically achieved by a forward viewing endoscope. Once the OCT data has been captured through the fiber core portion, it can be rendered and viewed from any angle and color based on the spectroscopic signals obtained.

Figure 15:
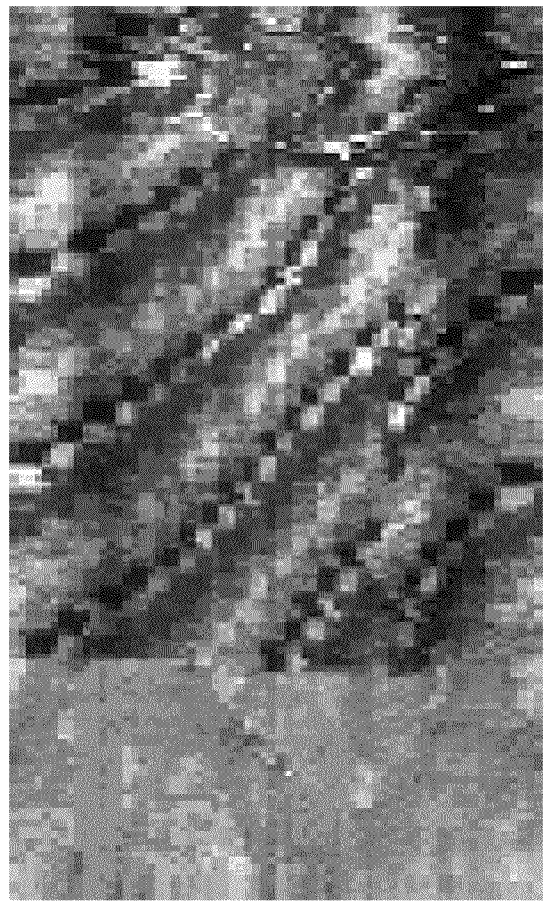
FIG. 15 shows a calibrated spectroscopic image constructed in accordance with an illustrative embodiment of the invention.

Because the optics often exhibit chromatic aberration, some post-processing of the spectroscopic image is usually required to achieve accurate assessment. As shown previously in FIG. 10, the light collection efficiencies vary depending on the distance from the probe and the wavelengths. Because OCT is able to measure the distance from the probe to the sample accurately, it offers an opportunity to correct for this aberration by calibrating the spectroscopic image according to pre-recorded calibration curves. The image in FIG. 15, which is similar to the image in FIG. 10, shows a significant reduction in focusing artifacts after calibration for collection efficiency.

Figure 16:
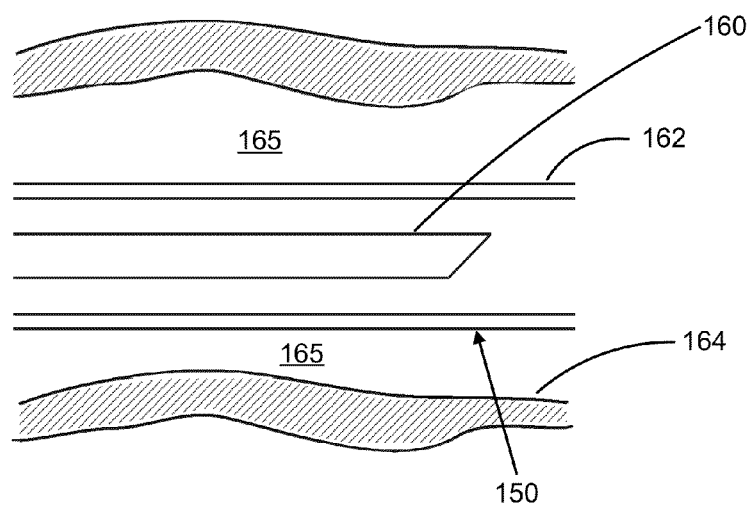
FIG. 16 is a schematic diagram of a catheter delivered imaging probe configured for spectroscopic imaging in accordance with an illustrative embodiment of the invention.

In vivo blood vessel imaging imposes a few additional requirements for combined spectroscopic and OCT imaging according to the present invention. Because the blood is not transparent, the blood has to be displaced to obtain accurate imaging. The present invention enables simulation and rapid acquisition of OCT and spectroscopic data as blood is displaced by injecting a liquid flushing solution. For intravascular imaging, data is collected with a catheter with internal optics that can be rotated rapidly and pulled back within a transparent outer sheath. FIG. 16 illustrates the major structures that lie in the optical path at the imaging locus in a catheter that is compatible with both spectroscopic and OCT imaging. The catheter 150 may include an imaging fiber 160, accessory optics such as lens and prisms, and one or more layers of protective sheaths 162 (usually made of plastic or glass materials).

In one embodiment, the spaces between the walls of the sheaths and between the outermost sheath and the vessel wall 164 are filled with liquid. To reduce undesired back reflections as much as possible, it is important that the refractive index of materials in the optical path to be matched as closely as possible. The suitable liquid for filling gaps inside the catheter includes, but is not limited to silicone oil, glycerol, and radio-opaque contrast solution. Because its refractive index closely matches the refractive indices of plastic sheath material, the angiographic contrast solution is the preferred liquid for flushing blood from the lumen 165.

Figure 17A:
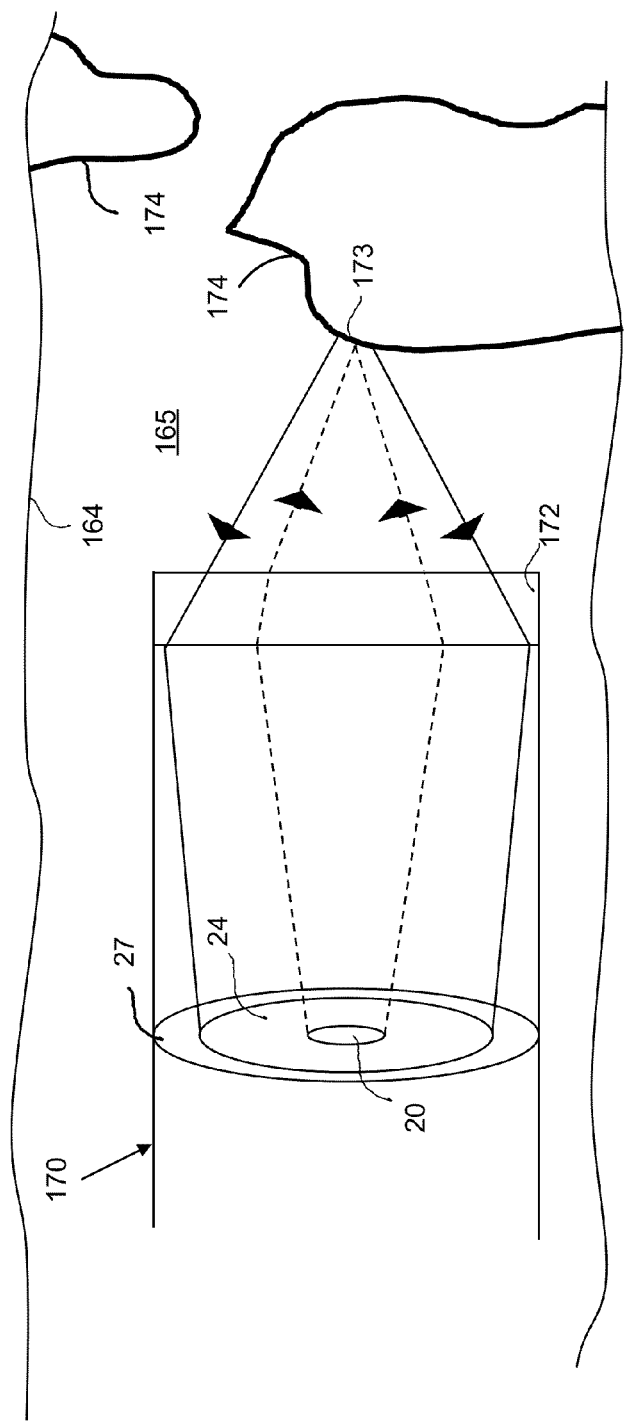
FIG. 17A is a schematic diagram of a forward scanning probe tip showing light propagation and scattering relative to a core and cladding in accordance with an illustrative embodiment of the invention.

FIG. 17A illustrates an imaging fiber 170 for an OCT imaging probe configured for spectroscopic signal collection. The imaging fiber or probe tip 170 is disposed in a lumen 165 having walls 164. Light from an optical source not shown is focused to a point or region 173. As shown, the fiber is configured for forward scanning such that it can image lumen objects 174 or material disposed in the lumen 165 such as plaques 174. A optical element 172, such as a lens, is in optical communication with the imaging fiber 170. The fiber 170 includes a core 20, a cladding 24, and a jacket 27. In some embodiments, jacket 27 is absent. Typically, the fiber core 20 is in optical communication with the light source, an interferometer and one or more detectors such as photodiode-based receivers or detectors.

As shown, by the light rays and arrows, light from the core 20, depicted as a dotted pair of lines, propagates from the core 20 and into the lumen 165 until reaching a focus 173 on lumen object 174. After the light from the core 20 is scattered from the lumen object 174, it is received by the core 20 and cladding 24. The returning scattered light is shown by the solid lines and arrows pointing to the cladding 24. The scattered light collected in the core can be used for OCT image generation. Similar, the scattered light entering the cladding can be used to generate a color map or color representation of the OCT data collected. The light used for color mapping the OCT data can be a plurality of different wavelengths sent simultaneously or narrowband of wavelengths or single wavelengths can be sent through the core sequentially and then collected by the cladding for processing and generating a color representation.

Figure 17B:
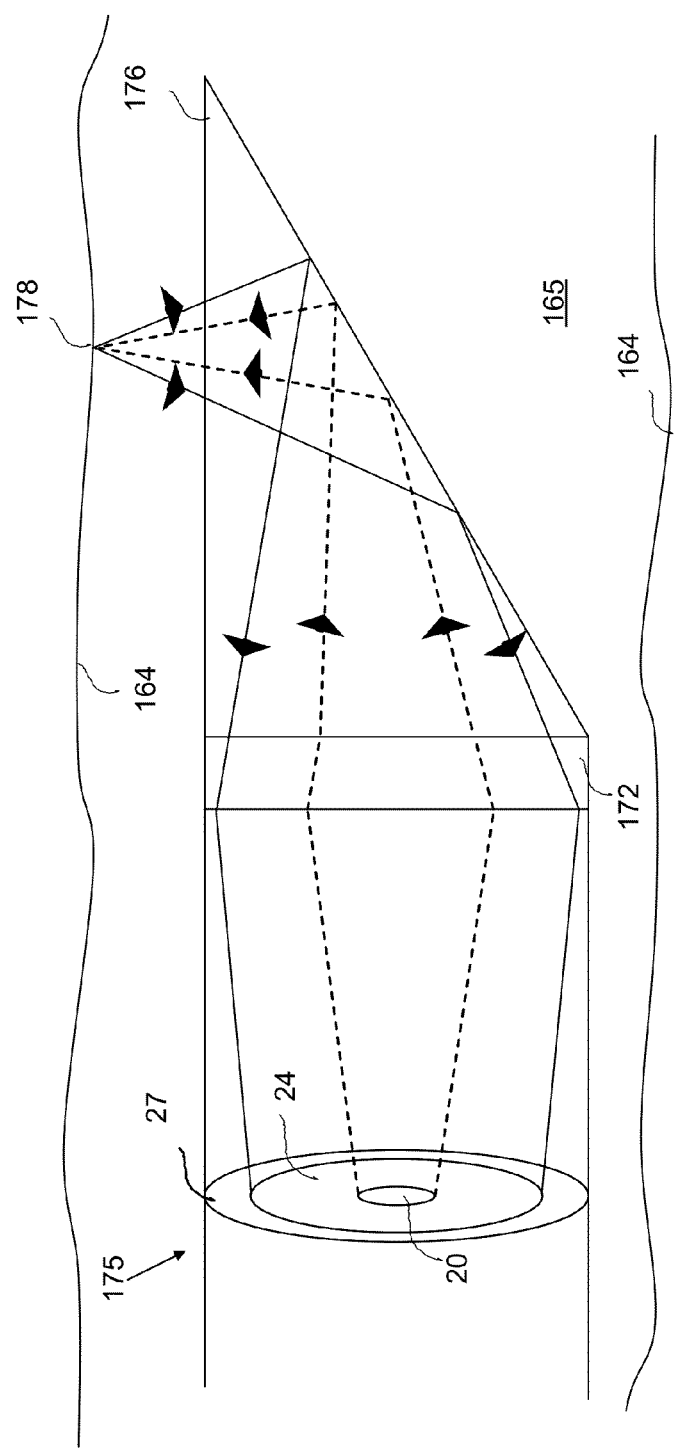
FIG. 17B is a schematic diagram of a side scanning probe tip showing light propagation and scattering relative to a core and cladding in accordance with an illustrative embodiment of the invention.

FIG. 17B illustrates another embodiment of an imaging fiber tip or probe tip 175 for an OCT imaging probe configured for spectroscopic signal collection. The imaging fiber 175 is disposed in a lumen 165 having walls 164. Light from a source (not shown) is focused to a point or region 178 on the lumen wall 164. As shown, the fiber or prove tip 175 is configured for side scanning such that it can image lumen objects 174 or material disposed in the lumen 165 such as plaques 174. A lens such as a grin lens or other optical element 172 is in optical communication with the imaging fiber tip 175. A beam director 176 is also use to direct the beam to the side such that the walls of the lumen 164 can be imaged. The fiber tip 175 includes a core 20, a cladding 24, and a jacket 27. In some embodiments, jacket 27 is absent. Typically, the fiber core 20 is in optical communication with the optical source, an interferometer and one or more detectors such as photo-diode-based receivers or detectors. The beam director or reflector 176 shown rotates with the fiber 175 such that OCT and spectroscopy data can be collected with respect to the lumen walls 174 and related substructures.

As shown, by the light rays and arrows, light from the core 20 depicted as ray spanning an area of the lumen, is identified as a dotted pair of lines that propagate from the core 20 and into the lumen 165 until reaching a focus 178 on lumen wall 164. After the light from the core 20 is scattered from the lumen wall 174, it is received by the core 20 and cladding 24 as shown by the solid lines and arrows point to the cladding 24. This light propagates along the imaging fiber portion 175 until it is coupled out of a fiber portion from a cladding layer and through the outer surface of the fiber portion for spectroscopic processing. This unguided light, which has been reflected back and forth along the cladding boundary, is used for color information and not image formation. In contrast, the light traveling in the core continues until received by a detector in electrical or optical communication with an OCT subsystem. Once received, this guided light is used to generate images which can then be color indexed using the other signals from the cladding.

In the description, the invention is discussed in the context of rotating imaging or forward scanning probes; however, these embodiments are not intended to be limiting and those skilled in the art will appreciate that the invention can also be used for other types of imaging applications, including non-biological applications.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The aspects, embodiments, features, and examples disclosed herein are to be considered illustrative in all respects and are not intended to limit the invention, the scope of which is defined only by the claims. Other embodiments, modifications, and usages will be apparent to those skilled in the art without departing from the spirit and scope of the claimed invention.

What is claimed is:

1. A method of collecting optical coherence data and spectroscopic data from a sample comprising the steps of:
   transmitting light in an optical fiber core having a first index of refraction to the sample;
   receiving light scattered from the sample;
   transmitting scattered light from the sample having a first mode in the optical fiber core to a first detector;
   transmitting scattered light from the sample having a second mode in a first cladding layer having a second index of refraction to a second detector;
   generating an optical coherence tomography image using the scattered light from the sample having the first mode; and
   overlaying spectroscopic data on the optical coherence tomography image, the spectrographic data obtained using the scattered light from the sample having the second mode.

2. The method of claim 1 wherein the scattered light having the first mode and the scattered light having the second mode are transmitted coaxially in the optical fiber core and the first cladding layer, respectively.

3. The method of claim 1 wherein the step of transmitting light in the optical fiber core having the first index of refraction to the sample further comprises the step of rotating the optical fiber core.

4. The method of claim 1 wherein the scattered light having the second mode exits the first cladding layer at an angle before reaching the second detector.

5. The method of claim 1 wherein the optical coherence tomography image is a 3-D image and the spectroscopy data is a color representation of the sample.

6. The method of claim 1 further comprising the step of calibrating for collection efficiency such that the optical coherence tomography image is in focus.

7. A method of collecting optical coherence data and spectroscopic data from a sample comprising:
   transmitting light along a first optical fiber core to the sample;
   receiving light scattered from the sample at a second optical fiber core and an inner cladding, wherein the second optical fiber core and the inner cladding are concentrically arranged;
   transmitting scattered light from the sample having a first mode from the first optical fiber core to a first detector;
   transmitting scattered light from the sample having a second mode to a second detector; and
   generating an optical coherence tomography image of the sample having spectroscopic data overlaid thereon using the scattered light having the first mode and the scattered light having the second mode.

8. The method of claim 7 wherein the scattered light having the second mode exits the first cladding layer at an angle before reaching the second detector.

* * * * *